US011919832B2

(12) United States Patent
Lee et al.

(10) Patent No.: US 11,919,832 B2
(45) Date of Patent: Mar. 5, 2024

(54) DISSIMILAR METAL-SUPPORTED CATALYST FOR THE PRODUCTION OF AROMATICS BY METHANE DEHYDROAROMATIZATION AND METHOD FOR PRODUCING AROMATICS USING THE SAME

(71) Applicants: Korea University Research and Business Foundation, Seoul (KR); Seoul National University R&DB Foundation, Seoul (KR)

(72) Inventors: Kwan-Young Lee, Seoul (KR); Do Heui Kim, Seoul (KR); Jae Ik Sim, Seoul (KR); Byung Jin Lee, Seoul (KR)

(73) Assignees: Korea University Research and Business Foundation, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/194,379

(22) Filed: Mar. 8, 2021

(65) Prior Publication Data

US 2021/0275995 A1 Sep. 9, 2021

(30) Foreign Application Priority Data

Mar. 6, 2020 (KR) .................. 10-2020-0028336
Dec. 11, 2020 (KR) .................. 10-2020-0173305

(51) Int. Cl.
*C07C 2/76* (2006.01)
*B01J 23/89* (2006.01)
(Continued)

(52) U.S. Cl.
CPC ............. *C07C 2/76* (2013.01); *B01J 23/8906* (2013.01); *B01J 27/22* (2013.01); *B01J 29/068* (2013.01);
(Continued)

(58) Field of Classification Search
CPC ....................................................... C07C 2/76
See application file for complete search history.

(56) References Cited

U.S. PATENT DOCUMENTS

2014/0155258 A1  6/2014 Lauritzen et al.
2017/0266647 A1* 9/2017 Almutairi .............. B01J 29/072

FOREIGN PATENT DOCUMENTS

CN      110102336 A  *  8/2019  ............. B01J 29/48
DE   102014112436 A1  *  3/2016  ............. B01J 23/00
(Continued)

OTHER PUBLICATIONS

Machine translation CN 110102336. Accessed Jun. 8, 2022. (Year: 2022).*

(Continued)

*Primary Examiner* — In Suk C Bullock
*Assistant Examiner* — Alyssa L Cepluch
(74) *Attorney, Agent, or Firm* — NSIP Law

(57) ABSTRACT

Disclosed is a dissimilar metal-supported catalyst for the production of aromatics by methane dehydroaromatization. In the dissimilar metal-supported catalyst, a noble metal such as gold (Au), silver (Ag), platinum (Pt), and/or rhodium (Rh) is introduced into a catalyst supported with iron (Fe) on a zeolite support to promote the dehydrogenation of methane and the formation of iron carbide ($Fe_3C$) as an active species for dehydroaromatization, achieving a greatly improved yield of aromatics. Also disclosed is a method for producing aromatics using the dissimilar metal-supported catalyst.

5 Claims, 6 Drawing Sheets
(6 of 6 Drawing Sheet(s) Filed in Color)

(51) Int. Cl.
  *B01J 27/22* (2006.01)
  *B01J 29/068* (2006.01)
  *B01J 29/072* (2006.01)
  *B01J 29/44* (2006.01)
  *B01J 29/46* (2006.01)
  *B01J 29/72* (2006.01)

(52) U.S. Cl.
  CPC ............ *B01J 29/072* (2013.01); *B01J 29/44* (2013.01); *B01J 29/46* (2013.01); *B01J 29/7276* (2013.01); *B01J 2229/20* (2013.01); *C07C 2523/89* (2013.01)

(56) References Cited

FOREIGN PATENT DOCUMENTS

| WO | WO-2009124902 A1 * | 10/2009 | ............ B01J 29/068 |
|----|--------------------|---------|--------------------------|
| WO | WO2018/221704 A1   | 12/2018 | |

OTHER PUBLICATIONS

Machine translation WO 2009/124902. Retrieved Jun. 9, 2022 (Year: 2022).*

Machine translation DE 102014112436. Retrieved Jan. 6, 2023 (Year: 2023).*

Sim, Jae Ik et al., "Effect of co-catalyst on Fe/HZSM-5 catalyst for Direct Dehydroaromatization of Methane", *2019 KSIEC Spring Meeting*, Bexco, Busan, May 1-May 3, 2019 (pp. 1-3).

Sim, Jae Ik et al., "Promotional effect of Au on Fe/HZSM-5 catalyst for Methane Dehydroaromatization", *50th General Assembly & 47th IUPAC World Chemistry Congress*, Jul. 5-12, 2019 (pp. 1-3).

Sim, Jae Ik et al., "Promotional Effect of Au on Fe/HZSM-5 Catalyst for Methane Dehydroaromatization", *KIChE Fall Meeting and International Symposium*, Oct. 23, 2019-Oct. 25, 2019 (pp. 1-3).

Kojima, Ryoichi, et al. "Promotion effects of Pt and Rh on catalytic performances of Mo/HZSM-5 and Mo/HMCM-22 in selective methane-to-benzene reaction." *Catalysis letters* 110.1 (Apr. 21, 2006): pp. 15-21.

Denardin, Felipe et al. "Tuning the acidity and reducibility of Fe/ZSM-5 catalysts for methane dehydroaromatization." *Fuel 236* (Sep. 28, 2018): pp. 1293-1300.

Korean Office Action dated May 17, 2022 in corresponding Korean Patent Application No. 10-2020-0173305 (5 pages in Korean).

* cited by examiner

DISSIMILAR METAL-SUPPORTED CATALYST FOR THE PRODUCTION OF AROMATICS BY METHANE DEHYDROAROMATIZATION AND METHOD FOR PRODUCING AROMATICS USING THE SAME

CROSS-REFERENCE TO RELATED APPLICATIONS

This application claims the benefit under 35 USC § 119(a) of Korean Patent Application No. 10-2020-0028336 filed on Mar. 6, 2020 and Korean Patent Application No. 10-2020-0173305 filed on Dec. 11, 2020 in the Korean Intellectual Property Office, the entire disclosure of which is incorporated herein by reference for all purposes.

BACKGROUND OF THE INVENTION

1. Field of the Invention

The present invention relates to a dissimilar metal-supported catalyst for the production of aromatics by methane dehydroaromatization and a method for producing aromatics using the supported catalyst.

2. Description of the Related Art

Aromatics typified by benzene, toluene, and xylene are industrially very important compounds and are used as intermediates of chemical products, solvents, and raw materials for polymers. Approximately 40 million tons of benzene and 14 million tons of toluene were produced in 2012 and the demand for benzene and toluene is predicted to increase by 35% to 40% compared to the global GDP growth rate.

High value-added aromatics are currently being produced by catalytic naphtha reforming processes, which are mostly dependent on crude oil. However, such crude oil-dependent production processes have limitations in that they are greatly affected by sudden fluctuations in crude oil prices and limited crude oil reserves. Thus, there is a need to develop a technique for producing aromatics from a new raw material that departs from previous crude oil-dependent production approaches.

The recent development of shale gas extraction technologies such as horizontal drilling and hydraulic fracturing has led to low extraction costs for shale gas, creating significant changes in the global energy market. Natural gas (including shale gas) is composed of about 85% methane, about 10% ethane, and other light hydrocarbons such as propane. Considering the enormous reserves of natural gas (including shale gas), synthesis of high value-added compounds from natural gas is industrially very important. Recent research has focused on techniques for synthesizing high value-added compounds such as olefins and aromatics from natural gas components.

Particularly, many methods for synthesizing aromatics by methane dehydroaromatization have been intensively studied because they are economically advantageous compared to conventional methods for synthesizing aromatics from crude oil in that the price of the raw material is low. Methane dehydroaromatization requires a temperature of at least 700° C. and an appropriate catalyst for conversion to aromatics under nonoxidative conditions. The catalyst is required to have components such as metal active sites capable of activating the reactant methane, Brønsted acid sites capable of oligomerization and aromatization of the activated methane species, and a molecular sieve of an appropriate size (~0.5 nm) to selectively separate the aromatics. Methane dehydroaromatization essentially includes activation of the reactant by dehydrogenation and oligomerization/aromatization of the activated species.

Supported catalysts based on HZSM-5 supported with molybdenum (Mo) as an active metal have been widely used so far for methane dehydroaromatization but have limitations in that the yield of aromatics does not reach a satisfactory level.

SUMMARY OF THE INVENTION

The present invention has been made in an effort to solve the above-described problems and intends to provide a dissimilar metal-supported catalyst in which a noble metal such as gold (Au), silver (Ag), platinum (Pt), and/or rhodium (Rh) is further introduced into a catalyst supported with iron (Fe) as an active metal to promote the dehydrogenation of methane and the formation of iron carbide as an active species for dehydroaromatization, achieving an improved yield of aromatics. The present invention also intends to provide a method for producing aromatics using the supported catalyst.

One aspect of the present invention provides a dissimilar metal-supported catalyst including a zeolite support, iron (Fe) as a first metal supported on the zeolite support, and at least one metal selected from the group consisting of gold (Au), silver (Ag), platinum (Pt), and rhodium (Rh) as a second metal supported on the zeolite support wherein the dissimilar metal-supported catalyst is used for methane dehydroaromatization to aromatics.

According to the present invention, the first metal may be supported in an amount of 0.5 to 4% by weight, based on the total weight of the zeolite support.

According to the present invention, the second metal may be supported in an amount of 0.5 to 2% by weight, based on the total weight of the zeolite support.

According to the present invention, the iron (Fe) may be converted to iron carbide ($Fe_3C$) during the methane dehydroaromatization.

According to the present invention, the zeolite support may be selected from the group consisting of HZSM-5, ZSM-5, MCM-22, and MCM-41.

According to the present invention, the ratio Si/Al in the zeolite support may be 15 to 140.

A further aspect of the present invention provides a method for producing aromatics including dehydroaromatizing methane as a reactant in the presence of the dissimilar metal-supported catalyst.

According to the present invention, the reaction may be performed in a gas phase reactor including a column filled with the dissimilar metal-supported catalyst.

According to the present invention, the reactant may further include argon gas.

According to the present invention, the reaction may be performed at 600 to 800° C.

According to the present invention, the aromatics may be selected from the group consisting of benzene, toluene, xylene, naphthalene, and coke.

In the dissimilar metal-supported catalyst of the present invention, a noble metal such as gold (Au), silver (Ag), platinum (Pt), and/or rhodium (Rh) is introduced into a catalyst supported with iron (Fe) to promote the dehydrogenation of methane and the formation of iron carbide as an active species for dehydroaromatization, achieving an improved yield of aromatics.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
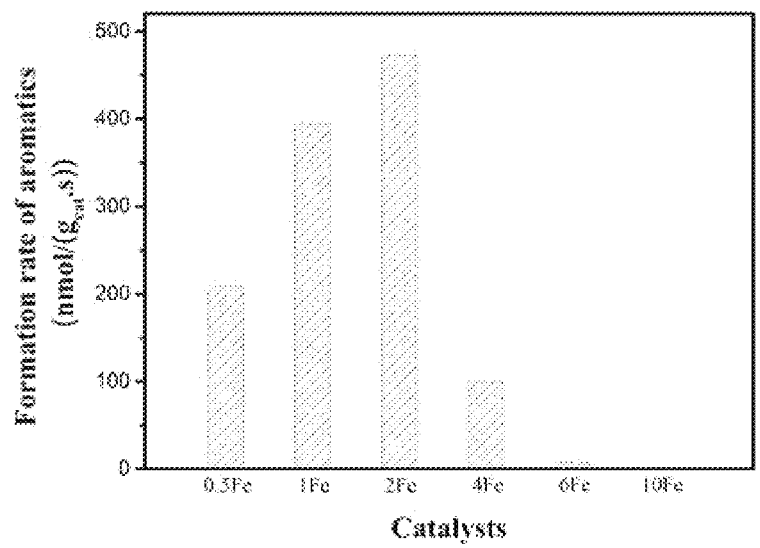
FIG. 1 shows the calculated formation rates of aromatics through methane dehydroaromatization according to the amount of iron supported.

Unless otherwise defined, all technical and scientific terms used herein have the same meaning as commonly understood by one of ordinary skill in the art to which this invention belongs. In general, the nomenclature used herein is well known and commonly employed in the art.

The present invention will now be described in more detail.

The present invention is directed to a dissimilar metal-supported catalyst for the production of aromatics by methane dehydroaromatization. Specifically, the present invention intends to provide a dissimilar metal-supported catalyst in which a metal such as gold (Au), silver (Ag), platinum (Pt), and/or rhodium (Rh) is further introduced into a catalyst supported with iron (Fe) as an active metal on a zeolite support to promote the dehydrogenation of methane, with the result that the formation of iron carbide is promoted, achieving an improved yield of aromatics.

More specifically, the present invention provides a dissimilar metal-supported catalyst including a zeolite support, iron (Fe) as a first metal supported on the zeolite support, and at least one metal selected from the group consisting of gold (Au), silver (Ag), platinum (Pt), and rhodium (Rh) as a second metal supported on the zeolite support wherein the dissimilar metal-supported catalyst is used for methane dehydroaromatization to aromatics.

The first metal and the second metal can be supported by suitable methods known in the art, preferably an incipient wetness impregnation method.

The following Examples section reveals that the first metal iron is preferably supported in an amount ranging from 0.5 to 4% by weight, based on the total weight of the zeolite support. Within this range, the supported first metal promotes the dehydrogenation of methane, resulting in a significant increase in the formation rate of aromatics.

The following Examples section reveals that the second metal is preferably supported in an amount of 0.5 to 2% by weight, based on the total weight of the zeolite support. The use of the second metal in an amount less than the lower limit or exceeding the upper limit has little or no effect in promoting the dehydrogenation of methane during the methane dehydroaromatization, leading to a significant reduction in the yield of final products (i.e. aromatics).

The zeolite support used in the supported catalyst of the present invention may be any of those commonly used as catalyst supports in the art. For example, the zeolite support may be selected from the group consisting of HZSM-5, ZSM-5, MCM-22, and MCM-41.

The ratio Si/Al in the zeolite support is preferably 15 to 140.

The present invention also provides a method for producing aromatics including dehydroaromatizing methane as a reactant in the presence of the dissimilar metal-supported catalyst.

The dehydroaromatization is preferably performed in a gas phase reactor including a column filled with the dissimilar metal-supported catalyst, for example, in a fixed bed gas phase reactor.

The reactant for the dehydroaromatization may further include argon gas in addition to methane.

The dehydroaromatization is preferably performed at 600 to 800° C.

The aromatics as the dehydroaromatization products may be selected from the group consisting of benzene, toluene, xylene, naphthalene, and coke.

The following Examples section reveals that the dehydroaromatization of the reactant methane in the presence of the dissimilar metal-supported catalyst is most preferably performed using a mixture of methane and argon in a 2:1 volume ratio at a GHSV of 4,500 ml/h·$g_{cat}$ and 750° C. for 1 hour.

The present invention will be explained in more detail with reference to the following examples. It will be appreciated by those skilled in the art that these examples are merely illustrative and the scope of the present invention is not construed as being limited to the examples. Thus, the true scope of the present invention should be defined by the appended claims and their equivalents.

Preparative Example 1. Preparation of Zeolite Catalysts Supported with Different Amounts of Iron First, $NH_4$-ZSM-5 with ammonium cations (CBV 3024E, Zeolyst) was heated at a rate of 5° C./min and calcined at 500° C. for 5 h to obtain a zeolite support HZSM-5 with protons, which was used as a catalyst support.

Next, different amounts (0.036, 0.072, 0.145, 0.29, 0.435, and 0.725 g) of iron nitrate hydrate ($Fe(NO_3)_3 \cdot 9H_2O$, Sigma-Aldrich) were separately dissolved in distilled water, supported on 1.0 g of the support HZSM-5 by an incipient wetness impregnation method, dried at 110° C. for 12 h, heated at a rate of 5° C./min under normal air conditions, and calcined at 500° C. for 5 h to prepare zeolite catalysts supported with different amounts (0.5, 1, 2, 4, 6, and 10 wt. %) of iron, based on the weight of the support (0.5Fe/HZSM-5, 1 Fe/HZSM-5, 2Fe/HZSM-5, 4Fe/HZSM-5, 6Fe/HZSM-5, and 10Fe/HZSM-5), respectively.

Preparative Example 2. Preparation of Gold-Supported Catalyst, Silver-Supported Catalyst, Platinum-Supported Catalyst and Rhodium-Supported Catalyst on the Iron-Supported Zeolite Catalyst Preparative Example 2-1. Preparation of Silver-Supported Catalyst, Platinum-Supported Catalyst and Rhodium-Supported Catalyst on the Iron-Supported Zeolite Catalyst The iron (2 wt. %)-supported zeolite catalyst prepared in Preparative Example 1 was dried at 110° C. for 12 h. Next, 0.0079 g of silver nitrate ($AgNO_3$, Sigma-Aldrich), 0.0086 g of platinum chloride ($PtCl_4$, Sigma-Aldrich), and 0.0080 g of rhodium nitrate ($Rh(NO_3)_3 \cdot xH_2O$, Sigma-Aldrich, ~36%) were separately dissolved in distilled water, supported on 1.0 g of the iron-supported HZSM-5 by an incipient wetness impregnation method, dried at 110° C. for 12 h, heated at a rate of 5° C./min under normal air conditions, and calcined at 500° C. for 5 h to prepare zeolite catalysts supported with 0.5 wt. % of silver, 0.5 wt. % of platinum, and 0.5 wt. % of rhodium together with 2 wt. % of iron, based on the weight of the support (2Fe-0.5Ag/HZSM-5, 2Fe-0.5Pt/HZSM-5, and 2Fe-0.5Rh/HZSM-5), respectively.

Preparative Example 2-2. Preparation of Catalysts Supported with Different Amounts of Gold on the Iron-Supported Zeolite Catalyst The iron (2 wt. %)-supported zeolite catalyst prepared in Preparative Example 1 was dried at 110° C. for 12 h. Next, different amounts (0.002 g, 0.001 g, 0.02 g, 0.03 g, 0.04 g, and 0.06 g) of gold chloride trihydrate (Au(III)Cl trihydrate, Sigma-Aldrich) were separately dissolved in distilled water, supported on 1.0 g of the iron-supported HZSM-5 by an incipient wetness impregnation method, dried at 110° C. for 12 h, heated at a rate of 5° C./min under normal air conditions, and calcined at 500° C. for 5 h to prepare zeolite catalysts supported with 2 wt. % of iron and different amounts (0.1, 0.5, 1, 1.5, 2, and 3 wt. %) of gold, based on the weight of the support (2Fe-0.1Au/HZSM-5, 2Fe-0.5Au/HZSM-5, 2Fe-1Au/HZSM-5, 2Fe-1.5Au/HZSM-5, 2Fe-2Au/HZSM-5, and 2Fe-3Au/HZSM-5), respectively.

Experimental Example 1. Production of Aromatics Through Methane Dehydroaromatization According to Amount of Iron Supported Aromatics were produced by methane dehydroaromatization using the catalysts prepared in Preparative Example 1. Specifically, 0.2 g of each of the catalysts prepared in Preparative Example 1 was filled in a fixed bed gas phase reactor having an outer diameter of 6.35 mm and heated to a reaction temperature of 750° C. in an ultrahigh purity argon gas (99.999%) atmosphere. When the reaction temperature was reached, the argon gas was replaced by a mixture of methane and argon (2:1, v/v) as a reaction gas. The reaction was allowed to proceed for 1 h under a flow of the reaction gas at a rate of 15 ml/min. The reactants and final products having passed through the catalyst bed of the fixed bed reactor were injected into a gas chromatograph connected on-line to the fixed bed reactor while maintaining a temperature of 230° C. Gas components were analyzed by the gas chromatography and used to calculate the formation rates of aromatics as the products. The results are shown in FIG. 1.

Referring to FIG. 1, the formation rates of aromatics through dehydroaromatization were significantly high when the amounts of the supported iron were 0.5-4 wt. % compared to those when the amounts of the supported iron were 6 and 10 wt. %. Particularly, the highest formation rate of aromatics was observed when the amount of the supported iron was 2 wt. %.

Experimental Example 2. Analysis of XRD Patterns

Figure 2:
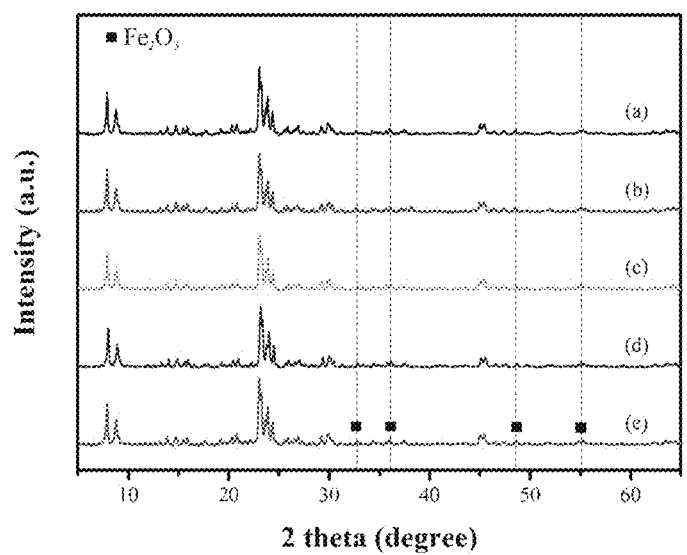
FIG. 2 shows XRD patterns of catalysts 2Fe/HZSM-5 (a), 2Fe-0.5Au/HZSM-5 (b), 2Fe-0.5Ag/HZSM-5 (c), 2Fe-0.5Pt/HZSM-5 (d), and 2Fe-0.5Rh/HZSM-5 (e)
Figure 3:
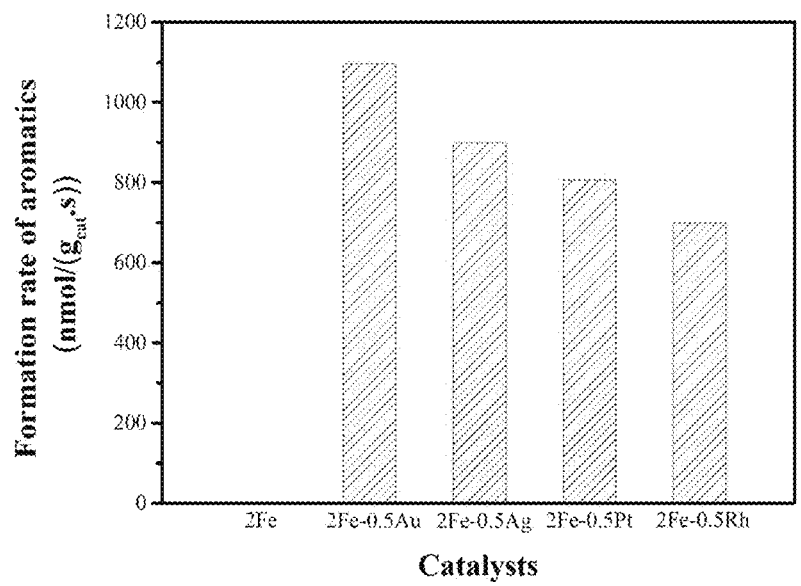
FIG. 3 shows the formation rates of aromatics in the initial stage of methane dehydroaromatization in the presence of different catalysts 2Fe/HZSM-5, 2Fe-0.5Au/HZSM-5, 2Fe-0.5Ag/HZSM-5, 2Fe-0.5Pt/HZSM-5, and 2Fe-0.5Rh/HZSM-5.
Figure 4:
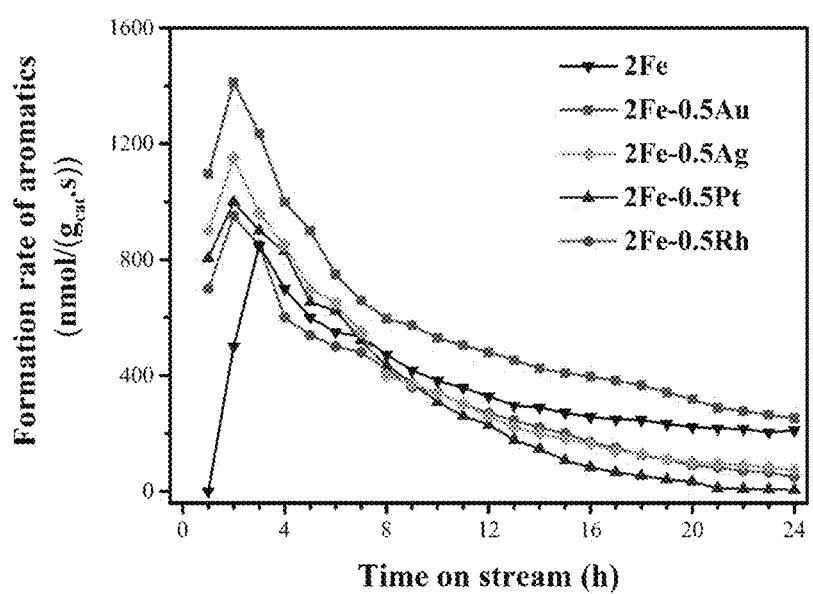
FIG. 4 shows the formation rates of aromatics through methane dehydroaromatization with time on stream in the presence of different catalysts 2Fe/HZSM-5, 2Fe-0.5Au/HZSM-5, 2Fe-0.5Ag/HZSM-5, 2Fe-0.5Pt/HZSM-5, and 2Fe-0.5Rh/HZSM-5.
Figure 5:
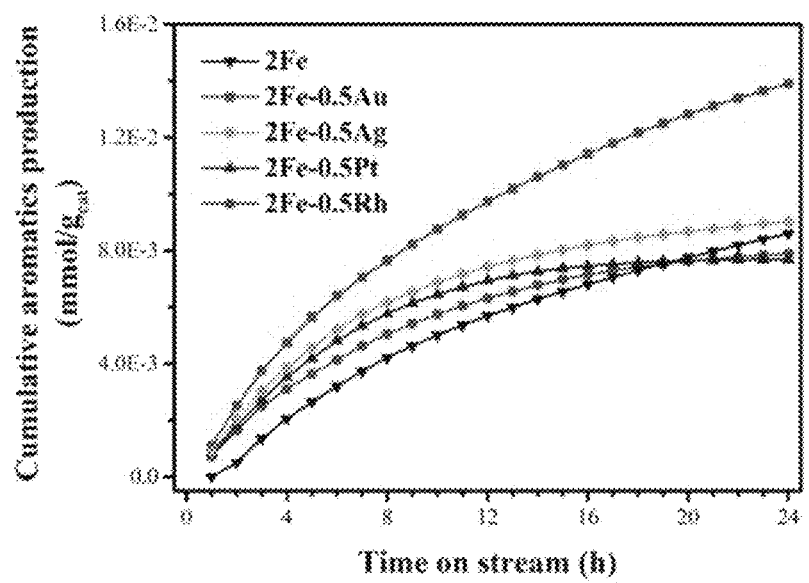
FIG. 5 shows the cumulative formation rates of aromatics through methane dehydroaromatization with time on stream in the presence of different catalysts 2Fe/HZSM-5, 2Fe-0.5Au/HZSM-5, 2Fe-0.5Ag/HZSM-5, 2Fe-0.5Pt/HZSM-5, and 2Fe-0.5Rh/HZSM-5.
Figure 6:
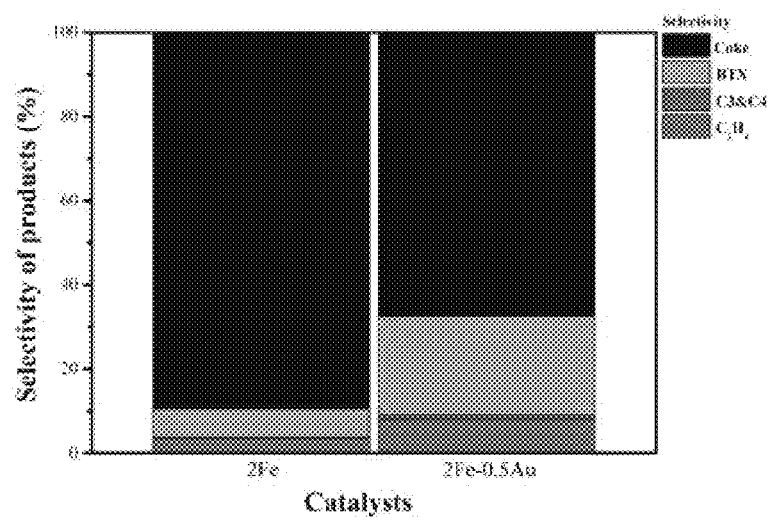
FIG. 6 shows the selectivities of catalysts 2Fe/HZSM-5 and 2Fe-0.5Au/HZSM-5 to aromatics and cock when methane dehydroaromatization was carried out using the catalysts.

FIG. 2 shows XRD patterns of the catalysts 2Fe/HZSM-5, 2Fe-0.5Au/HZSM-5, 2Fe-0.5Ag/HZSM-5, 2Fe-0.5Pt/HZSM-5, and 2Fe-0.5Rh/HZSM-5.

Referring to FIG. 2, the pattern of crystalline ZSM-5 was prominent in all of the catalysts. In addition, since the supported active metal iron was uniformly dispersed on the support, its peak was not distinct. No distinct peaks were observed for the gold-supported catalyst, the silver-supported catalyst, the platinum-supported catalyst, and the rhodium-supported catalyst due to the loading of small amounts of the noble metals.

Experimental Example 3. Production of Aromatics Through Methane Dehydroaromatization Using the Gold (Au)-Supported Catalyst, the Silver (Ag)-Supported Catalyst, the Platinum (Pt)-Supported Catalyst and the Rhodium (Rh)-Supported Catalyst on the Iron-Supported Zeolite Catalyst Aromatics were produced by methane dehydroaromatization using the iron (2 wt. %)-supported zeolite catalyst unsupported with a noble metal (2Fe/HZSM-5), the gold (0.5 wt. %)-supported catalyst (2Fe-0.5Au/HZSM-5), the silver (0.5 wt. %)-supported catalyst (2Fe-0.5Ag/HZSM-5), the platinum (0.5 wt. %)-supported catalyst (2Fe-0.5Pt/HZSM-5), and the rhodium (0.5 wt. %)-supported catalyst (2Fe-0.5Rh/HZSM-5). Specifically, 0.2 g of each of the supported catalysts was filled in a fixed bed gas phase reactor having an outer diameter of 6.35 mm and heated to a reaction temperature of 750° C. in an ultrahigh purity argon gas (99.999%) atmosphere. When the reaction temperature was reached, the argon gas was replaced by a mixture of methane and argon (2:1, v/v) as a reaction gas. The reaction was allowed to proceed for 1 h under a flow of the reaction gas at a rate of 15 ml/min. The reactants and final products having passed through the catalyst bed of the fixed bed reactor were injected into a gas chromatograph connected on-line to the fixed bed reactor while maintaining a temperature of 230° C. Gas components were analyzed by the gas chromatography and used to calculate the formation rates of aromatics as the products and the selectivity of the catalyst to the aromatics. The results are shown in FIGS. 3 to 6.

Referring to FIGS. 3 to 6, the use of the catalyst unsupported with a noble metal (2Fe/HZSM-5) did not lead to the production of aromatics due to carbonization in the initial stage of the reaction, whereas the formation rates of aromatics were ~1080.3 nmol/$g_{cat}$·s, ~875.3 nmol/$g_{cat}$·s, ~802.8 nmol/$g_{cat}$·s, and ~825.6 nmol/$g_{cat}$·s when the gold (0.5 wt. %)-supported catalyst (2Fe-0.5Au/HZSM-5), the silver (0.5 wt. %)-supported catalyst (2Fe-0.5Ag/HZSM-5), the platinum (0.5 wt. %)-supported catalyst (2Fe-0.5Pt/HZSM-5), and the rhodium (0.5 wt. %)-supported catalyst (2Fe-0.5Rh/HZSM-5) were used, respectively. The additional support with gold, silver, platinum or rhodium was found to significantly improve the formation rate of aromatics. Particularly, the highest formation rate of aromatics was found when gold was further supported. The selectivity of the catalyst unsupported with a noble metal (2Fe/HZSM-5) to aromatics was compared with that of the catalyst additionally supported with gold (2Fe-0.5Au/HZSM-5). As a result, the additional gold support was confirmed to increase the selectivity to aromatics from 6.65% to 23.5% and reduce the selectivity to coke from 89.47% to 67.56%. In conclusion, the inventive iron-supported zeolite catalyst additionally supported with gold, silver, platinum or rhodium significantly increases the formation rate of aromatics and the selectivity to aromatics and reduces the selectivity to coke.

Experimental Example 4.
CH$_4$-Temperature-Programmed Surface Reaction (CH$_4$-TPSR)

Figure 7:
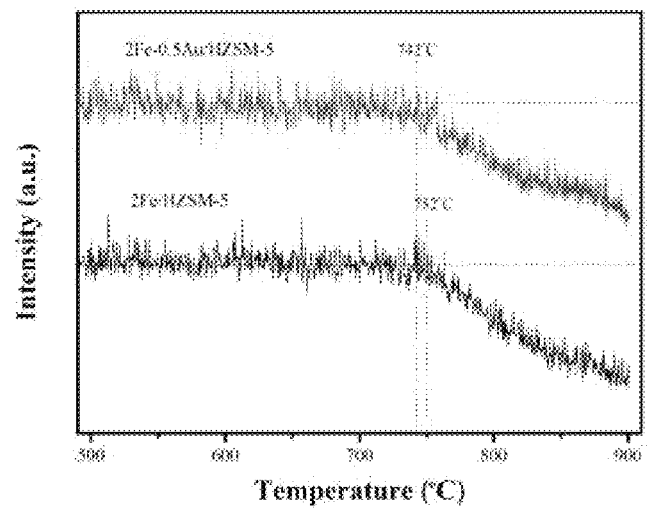
FIG. 7 shows the profiles of $CH_4$-TPSR of catalysts 2Fe/HZSM-5 and 2Fe-0.5Au/HZSM-5 for measuring the activation temperatures of methane.

FIG. 7 shows the profiles of CH$_4$-TPSR of the catalysts 2Fe/HZSM-5 and 2Fe-0.5Au/HZSM-5 for measuring the activation temperatures of methane.

Referring to FIG. 7, methane began to be activated at around 752° C. in the presence of the catalyst 2Fe/HZSM-5 supported with only iron, whereas methane was activated at a lower temperature of ~742° C. in the presence of the catalyst 2Fe-0.5Au/HZSM-5 supported with iron and gold, demonstrating that the loading of gold promoted the dehydrogenation of methane.

Experimental Example 5. X-Ray Photoelectron Spectroscopy (XPS)

Figure 8A:
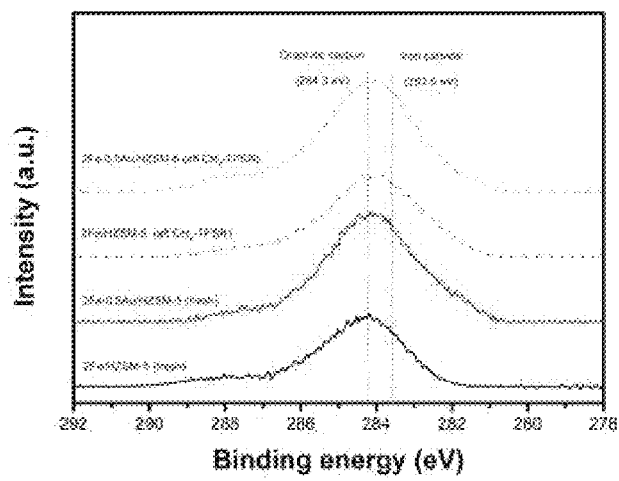
FIGS. 8A to 8C show XPS curves for C1s (FIG. 8A), Fe2p (FIG. 8B), and Au4f (FIG. 8C) orbitals of catalysts 2Fe/HZSM-5 and 2Fe-0.5Au/HZSM-5 before and after use for methane dehydroaromatization.
Figure 8B:
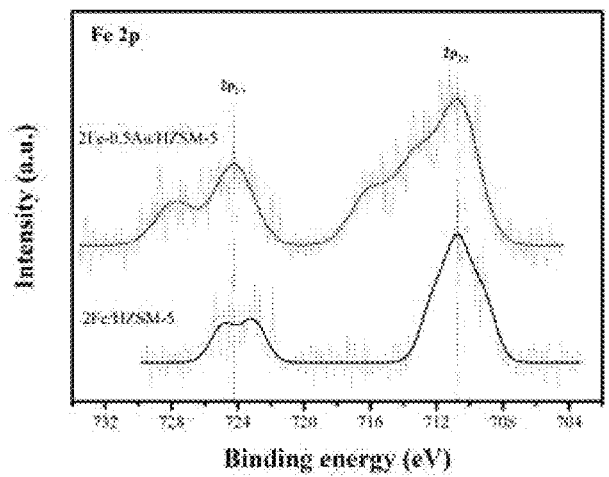
Figure 8C:
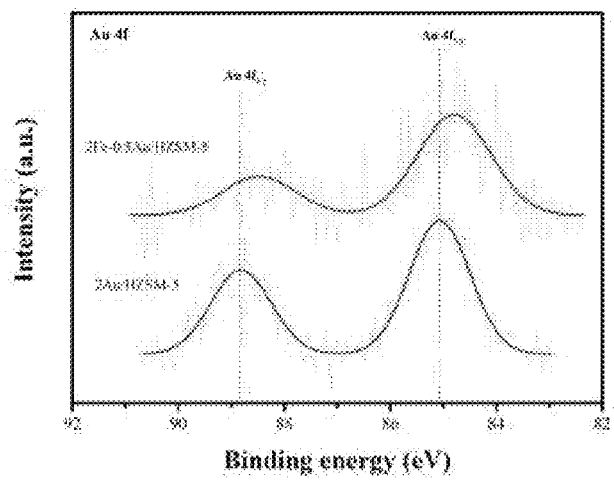

FIG. 8A to 8C show XPS curves for C1s (FIG. 8A), Fe2p (FIG. 8B), and Au4f (FIG. 8C) orbitals of the catalysts 2Fe/HZSM-5 and 2Fe-0.5Au/HZSM-5 before and after use for methane dehydroaromatization.

Referring to FIG. 8A to 8C, a higher degree of reduction to iron carbide (Fe$_3$C) was observed after the reaction in the presence of the catalyst 2Fe-0.5Au/HZSM-5 than in the presence of the catalyst 2Fe/HZSM-5. For the catalyst 2Fe-0.5Au/HZSM-5 in which gold (Au) was further supported on the catalyst 2Fe/HZSM-5, Fe became deficient in electrons due to the interaction between Fe and Au. This electron deficiency played a role in promoting the reduction of Fe to iron carbide (Fe$_3$C) during the reaction, leading to an improvement in the dehydrogenation ability of the catalyst.

In other words, the introduction of gold (Au) into the catalyst 2Fe/HZSM-5 caused Fe to be deficient in electrons due to the interaction between iron (Fe) and gold (Au) during methane dehydroaromatization, and as a result, the reduction of the electron-deficient Fe to iron carbide (Fe$_3$C) was promoted, markedly improving the yield of aromatics.

Experimental Example 6. Production of Aromatics Through Methane Dehydroaromatization According to Amount of Gold Supported Aromatics were produced by methane dehydroaromatization using the catalysts prepared in Preparative Example 2-2. Specifically, 0.2 g of each of the catalysts was filled in a fixed bed gas phase reactor having an outer diameter of 6.35 mm and heated to a reaction temperature of 750° C. in an ultrahigh purity argon gas (99.999%) atmosphere. When the reaction temperature was reached, the argon gas was replaced by a mixture of methane and argon (2:1, v/v) as a reaction gas. The reaction was allowed to proceed for 1 h under a flow of the reaction gas at a rate of 15 ml/min. The reactants and final products having passed through the catalyst bed of the fixed bed reactor were injected into a gas chromatograph connected on-line to the fixed bed reactor while maintaining a temperature of 230° C. Gas components were analyzed by the gas chromatography and used to calculate the formation rates of aromatics as the products. The results are shown in FIG. 9.

Figure 9:
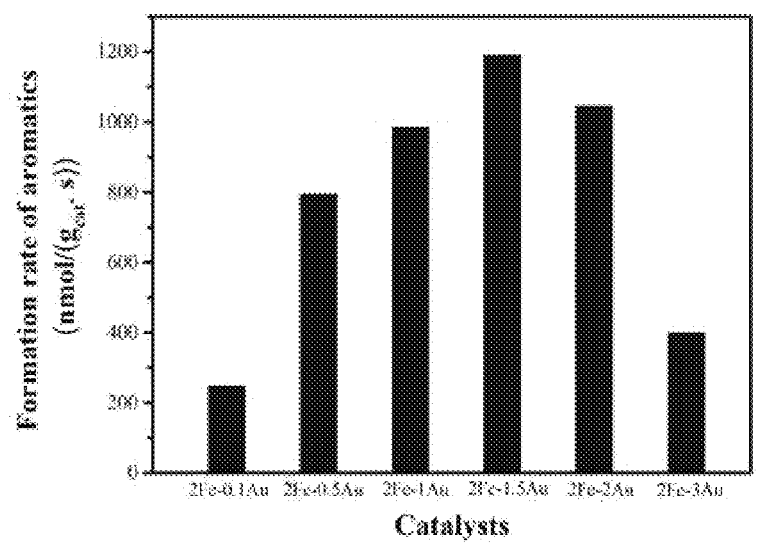
FIG. 9 shows the calculated formation rates of aromatics through methane dehydroaromatization according to the amount of gold supported.

Referring to FIG. 9, the formation rates of aromatics through dehydroaromatization were significantly high when the amounts of the supported gold were 0.5-2 wt. % compared to those when the amounts of the supported gold were 0.1 and 3 wt. %. Particularly, the highest formation rate of aromatics was observed when the amount of the supported gold was 1.5 wt. %.

Although the particulars of the present disclosure have been described in detail, it will be obvious to those skilled in the art that such particulars are merely preferred embodiments and are not intended to limit the scope of the present invention. Therefore, the true scope of the present invention is defined by the appended claims and their equivalents.

What is claimed is:

1. A method for producing aromatics comprising dehydroaromatizing methane as a reactant in the presence of a dissimilar metal-supported catalyst comprising a zeolite support, iron (Fe) as a first metal supported on the zeolite support, and at least one metal selected from the group consisting of gold (Au) and silver (Ag) as a second metal supported on the zeolite support, wherein the dissimilar metal-supported catalyst is used for methane dehydroaromatization to aromatics,
   wherein the first metal is supported in an amount of 0.5 to 4% by weight based on a total weight of the zeolite support.

2. The method according to claim 1, wherein the dehydroaromatizing is performed in a gas phase reactor comprising a column filled with the dissimilar metal-supported catalyst.

3. The method according to claim 1, wherein the reactant further comprises argon gas.

4. The method according to claim 1, wherein the dehydroaromatizing is performed at 600 to 800° C.

5. The method according to claim 1, wherein the aromatics are selected from the group consisting of benzene, toluene, xylene, and naphthalene.

* * * * *